United States Patent
Lee et al.

(10) Patent No.: US 10,746,272 B2
(45) Date of Patent: Aug. 18, 2020

(54) POWER TRANSMITTING DEVICE, MOTION ASSISTANCE APPARATUS, AND METHOD OF CONTROLLING THE MOTION ASSISTANCE APPARATUS

(71) Applicant: Samsung Electronics Co., Ltd., Suwon-si, Gyeonggi-do (KR)

(72) Inventors: Jongwon Lee, Suwon-si (KR); Youn Baek Lee, Yongin-si (KR); Se-Gon Roh, Suwon-si (KR); Jeonghun Kim, Suwon-si (KR); Minhyung Lee, Seoul (KR); Byungjune Choi, Gunpo-si (KR); Jungyun Choi, Suwon-si (KR); Hyun Do Choi, Yongin-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 440 days.

(21) Appl. No.: 15/468,473

(22) Filed: Mar. 24, 2017

(65) Prior Publication Data
US 2018/0066740 A1    Mar. 8, 2018

(30) Foreign Application Priority Data
Sep. 6, 2016  (KR) .................. 10-2016-0114604

(51) Int. Cl.
*F16H 37/08* (2006.01)
*A61F 5/01* (2006.01)
(Continued)

(52) U.S. Cl.
CPC ........... *F16H 37/0833* (2013.01); *A61F 2/68* (2013.01); *A61F 5/0102* (2013.01);
(Continued)

(58) Field of Classification Search
CPC ...... A61F 2002/6818; A61F 2002/6836; A61F 2002/6845; A61F 2002/6854;
(Continued)

(56) References Cited

U.S. PATENT DOCUMENTS 6,592,484 B1   7/2003   Tsai et al.
8,545,424 B2   10/2013  Hirata et al.
(Continued)

FOREIGN PATENT DOCUMENTS

DE   10 2013 202045 A1   8/2014
EP      2 982 884 A1      2/2016
(Continued)

OTHER PUBLICATIONS

Extended European Search Report issued by the European Patent Office dated Sep. 14, 2017 for corresponding EP Patent Application No. 17157204.3.

Primary Examiner — Jacob S. Scott
(74) Attorney, Agent, or Firm — Harness, Dickey and Pierce, P.L.C.

(57) ABSTRACT

Provided is a power transmitting device including an input side gear assembly that includes a single power input terminal and two power output terminals, an output side gear assembly that includes two power input terminals and a single power output terminal, the two power input terminals configured to operate using power received from the two power output terminals of the input side gear assembly, respectively, and a stopper module configured to block power to be transmitted through one of two power transmitting paths connecting the two power output terminals of the input side gear assembly and the two power input terminals of the output side gear assembly.

19 Claims, 16 Drawing Sheets

(51) Int. Cl.
*F16H 3/44* (2006.01)
*A61H 3/00* (2006.01)
*A61H 1/02* (2006.01)
*A61F 2/68* (2006.01)
*F16D 63/00* (2006.01)
*F16H 57/10* (2006.01)
*F16D 125/30* (2012.01)
*F16H 3/00* (2006.01)
*F16H 25/16* (2006.01)

(52) U.S. Cl.
CPC .............. *A61H 1/0244* (2013.01); *A61H 3/00* (2013.01); *F16D 63/006* (2013.01); *F16H 3/006* (2013.01); *F16H 3/44* (2013.01); *F16H 25/16* (2013.01); *A61F 2002/6836* (2013.01); *A61F 2005/0155* (2013.01); *A61F 2005/0158* (2013.01); *A61F 2005/0165* (2013.01); *A61H 2003/007* (2013.01); *A61H 2201/1215* (2013.01); *A61H 2201/1472* (2013.01); *A61H 2201/163* (2013.01); *A61H 2201/165* (2013.01); *A61H 2201/1621* (2013.01); *A61H 2201/1626* (2013.01); *A61H 2201/1642* (2013.01); *A61H 2201/1671* (2013.01); *A61H 2201/5061* (2013.01); *A61H 2201/5064* (2013.01); *A61H 2201/5071* (2013.01); *A61H 2201/5084* (2013.01); *A61H 2203/0406* (2013.01); *A61H 2205/108* (2013.01); *F16D 2125/30* (2013.01); *F16H 57/10* (2013.01)

(58) Field of Classification Search
CPC ...... A61F 2005/0155; A61F 2005/0158; A61F 2005/0165; A61F 2/68; A61F 5/0102; A61H 1/0244; A61H 2003/007; A61H 2201/1215; A61H 2201/1472; A61H 2201/1621; A61H 2201/1626; A61H 2201/163; A61H 2201/1642; A61H 2201/165; A61H 2201/1671; A61H 2201/5061; A61H 2201/5064; A61H 2201/5071; A61H 2201/5084; A61H 2203/0406; A61H 2205/108; A61H 3/00; F16D 2125/30; F16D 63/006; F16H 37/0833; F16H 3/006; F16H 3/44; F16H 57/10; F16H 2200/2007; F16H 2200/2035
See application file for complete search history.

(56) References Cited

U.S. PATENT DOCUMENTS

| | | | |
|---|---|---|---|
| 8,870,967 | B2 | 10/2014 | Herr et al. |
| 2007/0281822 | A1* | 12/2007 | Maier ................... B25B 21/00 475/286 |
| 2013/0305865 | A1 | 11/2013 | Howe et al. |
| 2015/0094186 | A1* | 4/2015 | Bang ....................... F16H 3/44 475/280 |
| 2015/0335514 | A1 | 11/2015 | Choi et al. |
| 2016/0038368 | A1* | 2/2016 | Lee ...................... A61H 1/0244 623/24 |
| 2016/0106615 | A1* | 4/2016 | Lee ......................... A61H 3/00 414/4 |
| 2016/0107309 | A1 | 4/2016 | Walsh et al. |
| 2017/0151865 | A1* | 6/2017 | Cho ........................ F16H 3/725 |

FOREIGN PATENT DOCUMENTS

| | | |
|---|---|---|
| JP | 4072095 B2 | 4/2008 |
| JP | 2012-143365 A | 8/2012 |
| JP | 5833480 B2 | 12/2015 |
| KR | 10-2016-0017953 A | 2/2016 |
| KR | 10-2016-0017969 A | 2/2016 |
| KR | 10-1605541 | 3/2016 |

\* cited by examiner

10

POWER TRANSMITTING DEVICE, MOTION ASSISTANCE APPARATUS, AND METHOD OF CONTROLLING THE MOTION ASSISTANCE APPARATUS

CROSS-REFERENCE TO RELATED APPLICATION

This application claims under 35 U.S.C. § 119 to Korean Patent Application No. 10-2016-0114604, filed on Sep. 6, 2016, in the Korean Intellectual Property Office, the entire contents of which are incorporated herein by reference in their entirety.

BACKGROUND

1. Field

At least one example embodiment relates to a power transmitting device, a motion assistance apparatus, and/or a method of controlling one or more of the power transmitting device and the motion assistance apparatus including same.

2. Description of the Related Art

A power transmitting device is a device configured to transmit power received from a driving source to another component, and may be used for various apparatuses, for example, motion assistance apparatuses enabling the elderly and/or patients having joint problems to walk with less effort, and motion assistance apparatuses increasing muscular strength of users for military purposes.

SUMMARY

Some example embodiments relate to a power transmitting device.

In some example embodiment, the power transmitting device may include an input side gear assembly including a first power input terminal and a plurality of first power output terminals; an output side gear assembly including a plurality of second power input terminals and a second power output terminal, the plurality of second power input terminals configured to operate based on power received from the plurality of first power output terminals of the input side gear assembly, respectively; and a stopper mechanism configured to block power transmission through one of two power transmitting paths connecting the plurality of first power output terminals and the plurality of second power input terminals.

In some example embodiment, the input side gear assembly comprises: an input side sun gear, the input sun gear being the first power input terminal; an input side planetary gear connected to an outer circumferential surface of the input side sun gear, the input side planetary gear configured to rotate based on power received from the input side sun gear; and an input side carrier and an input side ring gear each connected to the input side planetary gear, the input side carrier and the input side ring gear each being one of the plurality of first power output terminals.

In some example embodiment, the output side gear assembly comprises: an output side sun gear and an output side ring gear connected to the input side carrier and the input side ring gear, respectively, the output side sun gear and the output side ring gear each being one of the plurality of second power input terminals; an output side planetary gear configured to engage with the output side sun gear and the output side ring gear; and an output side carrier connected to a rotation axis of the output side planetary gear, and the output side carrier being the second power output terminal.

In some example embodiment, the output side sun gear includes a compound gear having first external teeth configured to engage with the output side planetary gear, and second external teeth configured to receive power transmitted from the input side carrier, the second external teeth having a greater diameter than the first external teeth.

In some example embodiment, the power transmitting device further includes a first connecting body configured to connect the input side carrier and the output side sun gear.

In some example embodiment, the input side ring gear has internal teeth configured to engage with the input side planetary gear, and external teeth configured to transmit power to the output side ring gear.

In some example embodiment, the power transmitting device further includes a second connecting body configured to connect the input side ring gear and the output side ring gear.

In some example embodiment, the stopper mechanism comprises: a first stopper configured to block power transmission through a first power transmitting path of the two power transmitting paths; and a second stopper configured to block power transmission through a second power transmitting path of the two power transmitting paths.

In some example embodiment, the first stopper is configured to operate in one of a first restraint state and a first release state, the first restraint state being a state in which the first stopper is configured to engage with at least one of a plurality of first power transmitting elements on the first power transmitting path, and the first release state being a state in which the first stopper is disengaged from the plurality of first power transmitting elements, and the second stopper is configured to operate in one of a second restraint state and a second release state, second restraint state being a state in which the second stopper is configured to engage with at least one of a plurality of second power transmitting elements disposed on the second power transmitting path, and the second release state being a state in which the second stopper is disengaged from the plurality of second power transmitting elements.

In some example embodiment, the stopper mechanism further comprises: a cam mechanism configured to, enable the second stopper to operate in the second release state in response to the first stopper operating in the first restraint state, and enable the second stopper to operate in the second restraint state in response to the first stopper operating in the first release state.

In some example embodiment, the first stopper is configured to switch between the first restraint state and the first release state and the second stopper is configured to switch between the second restraint state and the second release state in response to the cam mechanism rotating 90 degrees.

In some example embodiment, the cam mechanism comprises: a first cam configured to switch the first stopper between the first restraint state and the first release state; and a second cam configured to switch the second stopper between the second restraint state and the second release state.

In some example embodiment, the first cam and the second cam are configured to perform a single rigid body motion.

In some example embodiment, the first cam and the second cam are orthogonal to each other.

In some example embodiment, the first stopper and the second stopper each comprise a pair of pincers configured to rotate about a single center of rotation, and a pair of extensions extending from the pair of pincers, respectively, wherein the first cam is between the pair of extensions of the first stopper, and the second cam is between the pair of extensions of the second stopper.

In some example embodiment, the first stopper and the second stopper each further comprise an elastic member configured to provide elastic force to rotate the pair of pincers in opposite directions.

Some Example Embodiments Relate to a Motion Assistance Apparatus

In some example embodiment, the motion assistance apparatus includes a driving source configured to generate power; a first supporting member configured to support a first portion of a user; a second supporting member configured to support a second portion of the user; a power transmitting frame connected to the second supporting member, the power transmitting frame configured to rotate relative to the first supporting member; and a power transmitting device configured to transmit the power to the power transmitting frame, the power transmitting device including, an input side gear assembly including a first power input terminal and a plurality of first power output terminals, the first power input terminal configured to operate based on the power; an output side gear assembly including a plurality of second power input terminals each configured to operate based on the power received from a respective one of the plurality of first power output terminals, and a second power output terminal configured to transmit the power to the power transmitting frame; and a stopper mechanism configured to block power transmission through one of two power transmitting paths connecting the plurality of first power output terminals and the plurality of second power input terminals.

Some Example Embodiments Relate to a Method of Controlling a Motion Assistance Apparatus In some example embodiment, the method includes sensing motion information of a user; selecting one of a plurality of power transmitting paths of a power transmitting device as a selected power transmission path based on the motion information; and transmitting power through the selected power transmission path.

In some example embodiment, the method further includes determining a motion task based on the motion information, wherein the selecting is based on the motion task, the selecting including, selecting a power transmitting path with a low reduction ratio, among the plurality of power transmitting paths, as the selected power transmission path, if the motion task corresponds to level walking; and selecting a power transmitting path with a high reduction ratio, among the plurality of power transmitting paths, as the selected power transmission path, if the motion task corresponds to one of slope walking, standing, and sitting.

In some example embodiment, the method further includes determining a desired torque level based on the motion information, wherein the selecting is based on the desired torque level, the selecting including, selecting a power transmitting path with a low reduction ratio, among the plurality of power transmitting paths, as the selected power transmission path, if the desired torque level is less than a set torque; and selecting a power transmitting path with a high reduction ratio, among the plurality of power transmitting paths, as the selected power transmission path, if the desired torque level is greater than or equal to the set torque.

Some example embodiments relate to a power transmitting device.

In some example embodiments, the power transmitting device includes a first gear assembly including a first input gear and a plurality of first output gears; and a second gear assembly including a plurality of second input gears and a second output gear, the plurality of second input gears and the plurality of first output gears configured to connect via a selected transmission path of a plurality of transmission paths between the plurality of first output gears and the plurality of second input gears, each of the plurality of transmission paths having a different gear ratio associated therewith.

In some example embodiments, the power transmitting device further includes a cam connected to a stopping mechanism, the cam configured to rotate between a first position and a second position, the first position being a position in which the stopping mechanism engages with a first one of the plurality of second input gears and disengages from a second one of the plurality of second input gears, and the second position being a position in which the stopping mechanism is disengaged from the first one of the plurality of second input gears and engages with the second one of the plurality of second input gears.

Some example embodiments relate to a motion assistance apparatus.

In some example embodiments, the motion assistance apparatus includes the power transmitting device, the power transmitting device configured to provide an assistance force to portion of the user; a sensor configured to sense motion information associated with motion of the user; and a controller configured to determine one or more of a motion task and a desired torque level based on the motion information, and to adjust the assistance force by controlling the cam to move to one of the first position and the second position based on the one or more of the motion task and the desired torque level.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which.

DETAILED DESCRIPTION

Figure 1:
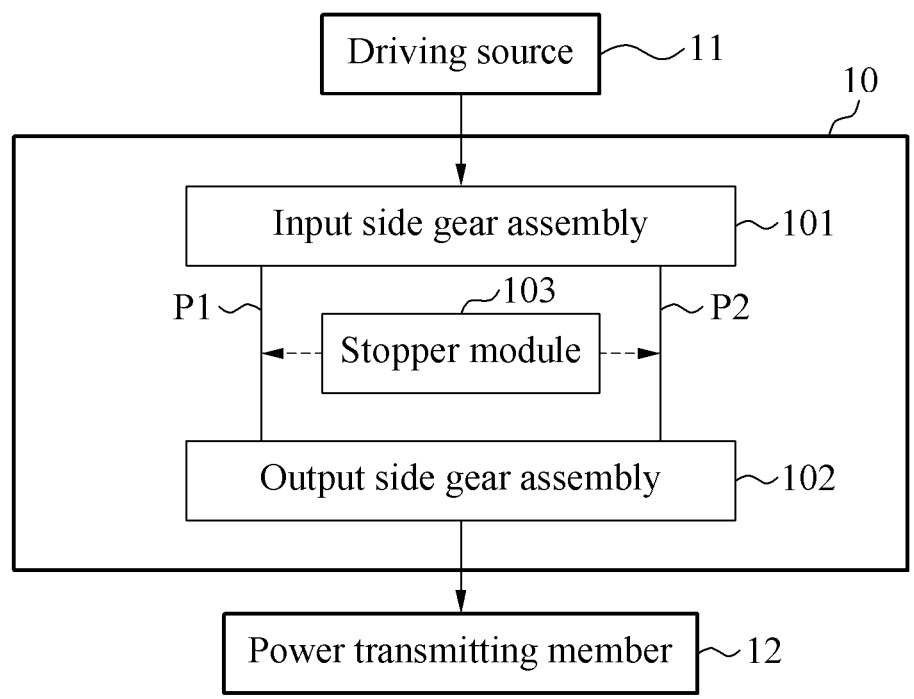
FIG. 1 is a block diagram illustrating a power transmitting device according to at least one example embodiment.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of example embodiments, detailed description of well-known related structures or functions will be omitted when it is deemed that such description will cause ambiguous interpretation of the present disclosure.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

FIG. 1 is a block diagram illustrating a power transmitting device according to at least one example embodiment.

Referring to FIG. 1, a power transmitting device 10 may transmit, to a power transmitting member 12 connected to a power output terminal, power received from a driving source 11 connected to a power input terminal. The power transmitting device 10 may include a plurality of power transmitting paths P1 and P2, and transmit the power received from the driving source 11 to the power transmitting member 12 through one of the plurality of power transmitting paths P1 and P2. The power transmitting device 10 may include an input side gear assembly 101 provided in a 3-port system structure including a single power input terminal and two power output terminals, an output side gear assembly 102 provided in a 3-port system structure including two power input terminals and a single power output terminal, and a stopper module 103 configured to block power to be transmitted through one of the plurality of power transmitting paths P1 and P2.

The first power transmitting path P1 of the plurality of power transmitting paths P1 and P2 may have a reduction ratio different from that of the second power transmitting path P2, for example, a relatively high reduction ratio. In this example, a state in which power is transmitted through the first power transmitting path P1 is referred to as a "high reduction ratio mode" or "low speed mode", and a state in which power is transmitted through the second power transmitting path P2 is referred to as a "low reduction ratio mode" or "high speed mode". The stopper module 103 may change a power transmitting path of the power transmitting device 10, thereby enabling selection of a reduction ratio appropriate for a situation.

The above structure may achieve various advantageous when compared to a power transmitting device having a single power transmitting path, that is, having the same reduction ratio at all times, and configured to adjust a speed by controlling revolutions per minute (rpm) of a driving source, that is, configured to implement the "low speed mode" and "high speed mode".

For example, in a case in which a great torque needs to be applied to the power transmitting member 12, the power transmitting device 10 may operate in the "high reduction ratio mode" through the first power transmitting path P1. In this example, the power is transmitted using a high reduction ratio. Thus, the great torque may be generated using a small and light-weighted motor as the driving source 11.

Further, in a case in which the power transmitting member 12 needs to operate at a fast speed, the power transmitting device 10 may operate in the "high speed mode" through the second power transmitting path P2. In this example, the power is transmitted using a low reduction ratio. Thus, although the driving source 11 operates at a relatively low rpm, the power transmitting member 12 may operate at a fast speed. In a case of using a motor as the driving source 11, the rpm of the motor may decrease, and thus voltage drop caused by a counter electromotive force of the motor may be reduced, which may enable operation using a battery with a relatively small capacity, whereby miniaturization and weight reduction may be achieved. Further, as the rpm of the motor decreases, noise generating by engaging components of the power transmitting device 10 may be reduced.

Meanwhile, using a movement of the power transmitting member 12 with respect to external force being applied thereto, the external force applied to the power transmitting member 12 may be sensed. In response to the power transmitting device 10 operating in the "low reduction ratio mode", the backdrivability of the power transmitting device 10 may increase. Thus, a capability of sensing an operating state of the entire product including the power transmitting device 10, for example, a motion assistance apparatus, or a motion state of a user using the motion assistance apparatus may improve.

As described above, the power transmitting device 10 may selectively transmit power through one of the plurality of power transmitting paths P1 and P2. Thus, a reduction ratio appropriate for a situation may be selected using the power transmitting device 10.

Figure 2:
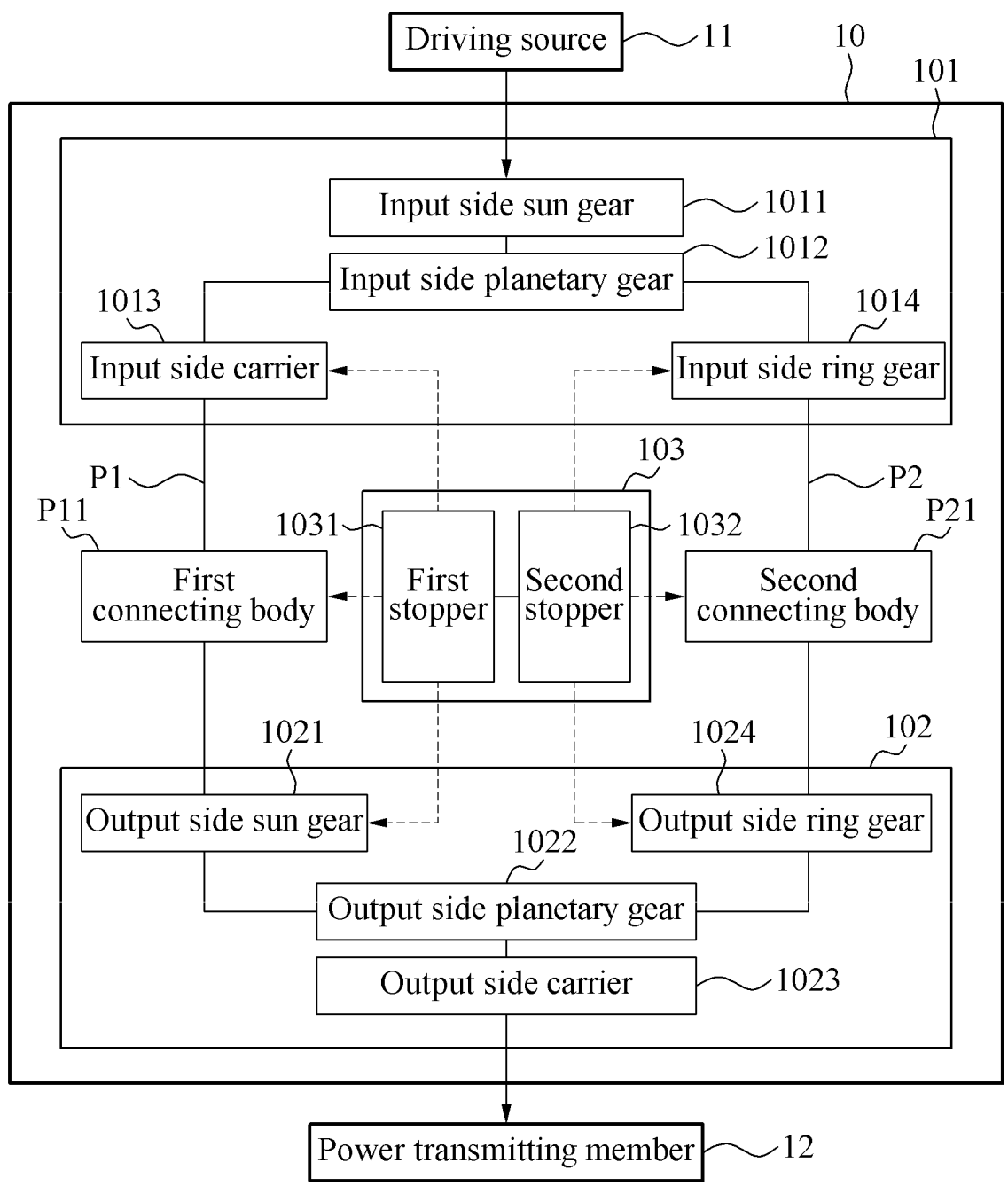
FIG. 2 is a block diagram illustrating a power transmitting device according to at least one example embodiment.
Figure 3:
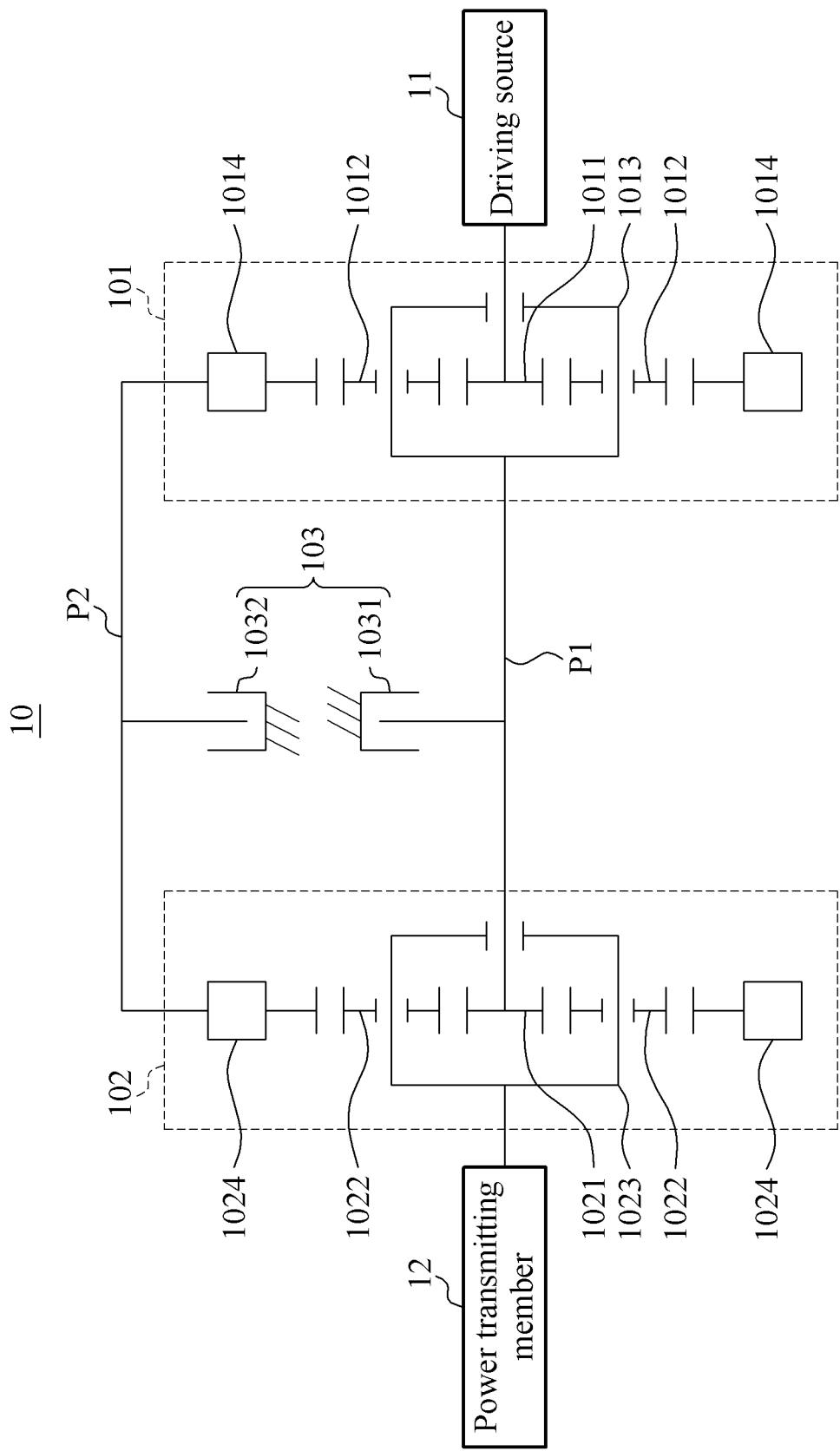
FIG. 3 is a diagram illustrating a power transmitting device according to at least one example embodiment.
Figure 4:
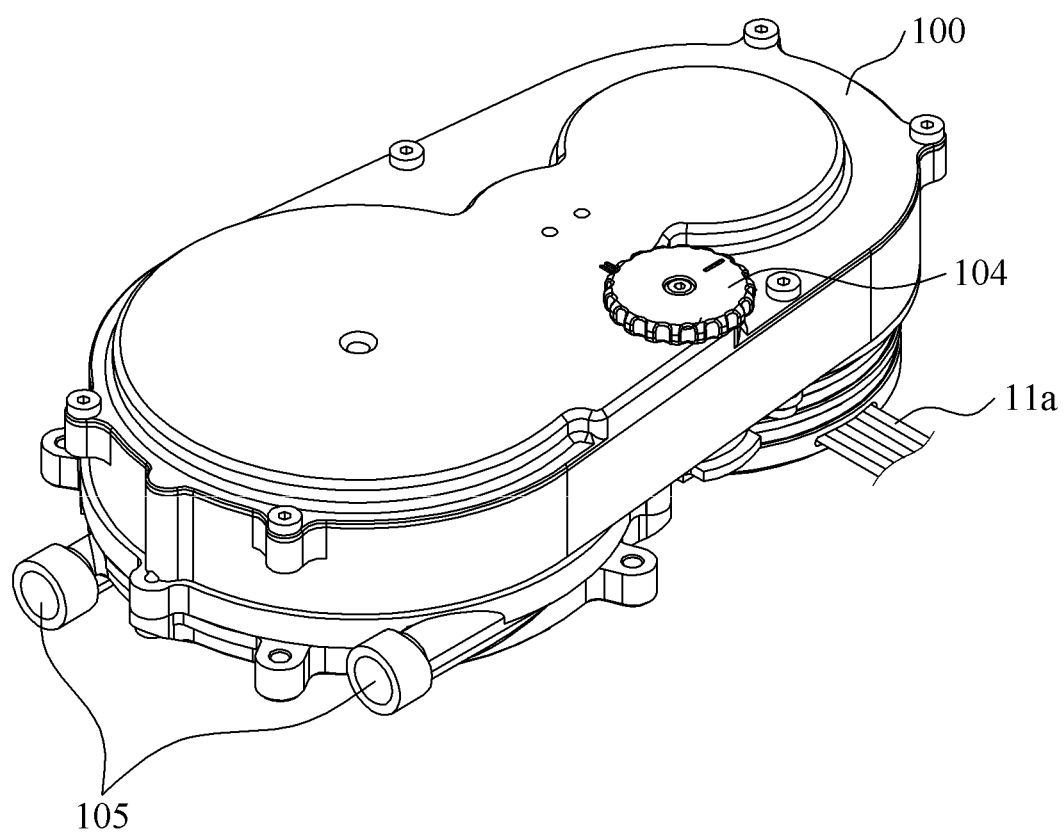
FIG. 4 is a perspective view illustrating a power transmitting device according to at least one example embodiment.
Figure 5:
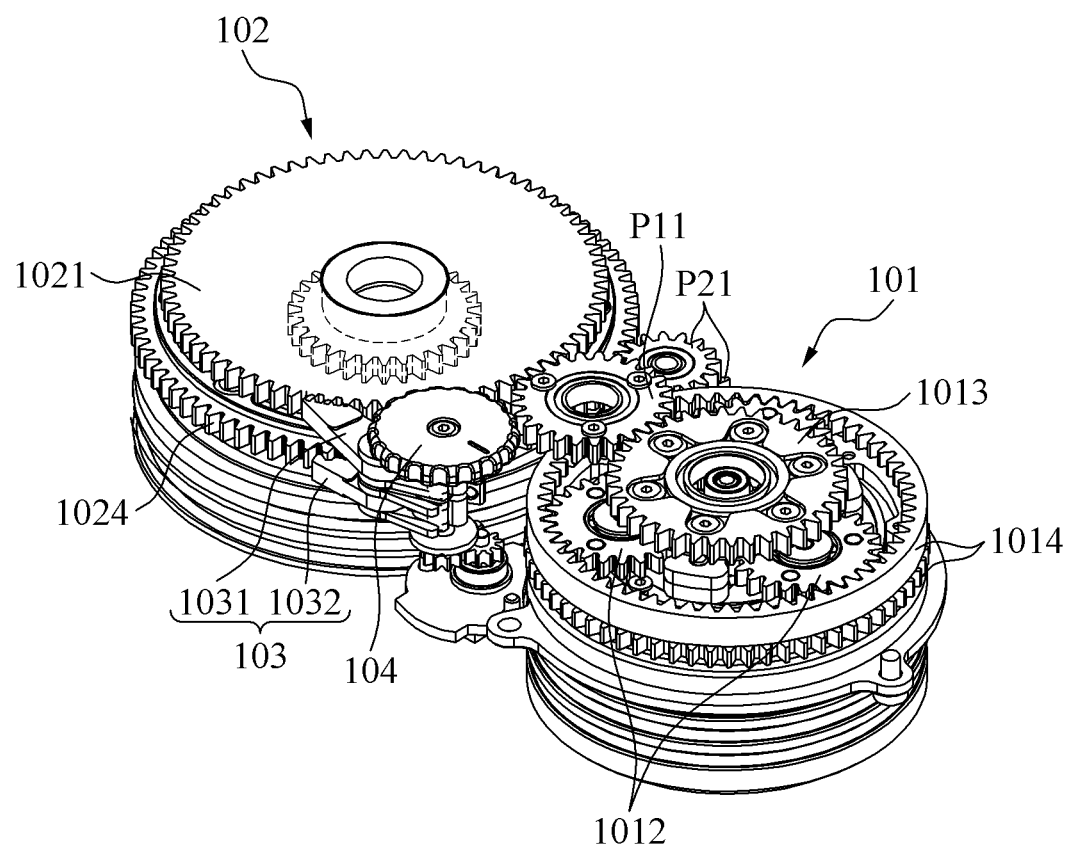
FIG. 5 is a perspective view illustrating an internal structure of a power transmitting device according to at least one example embodiment.
Figure 6:
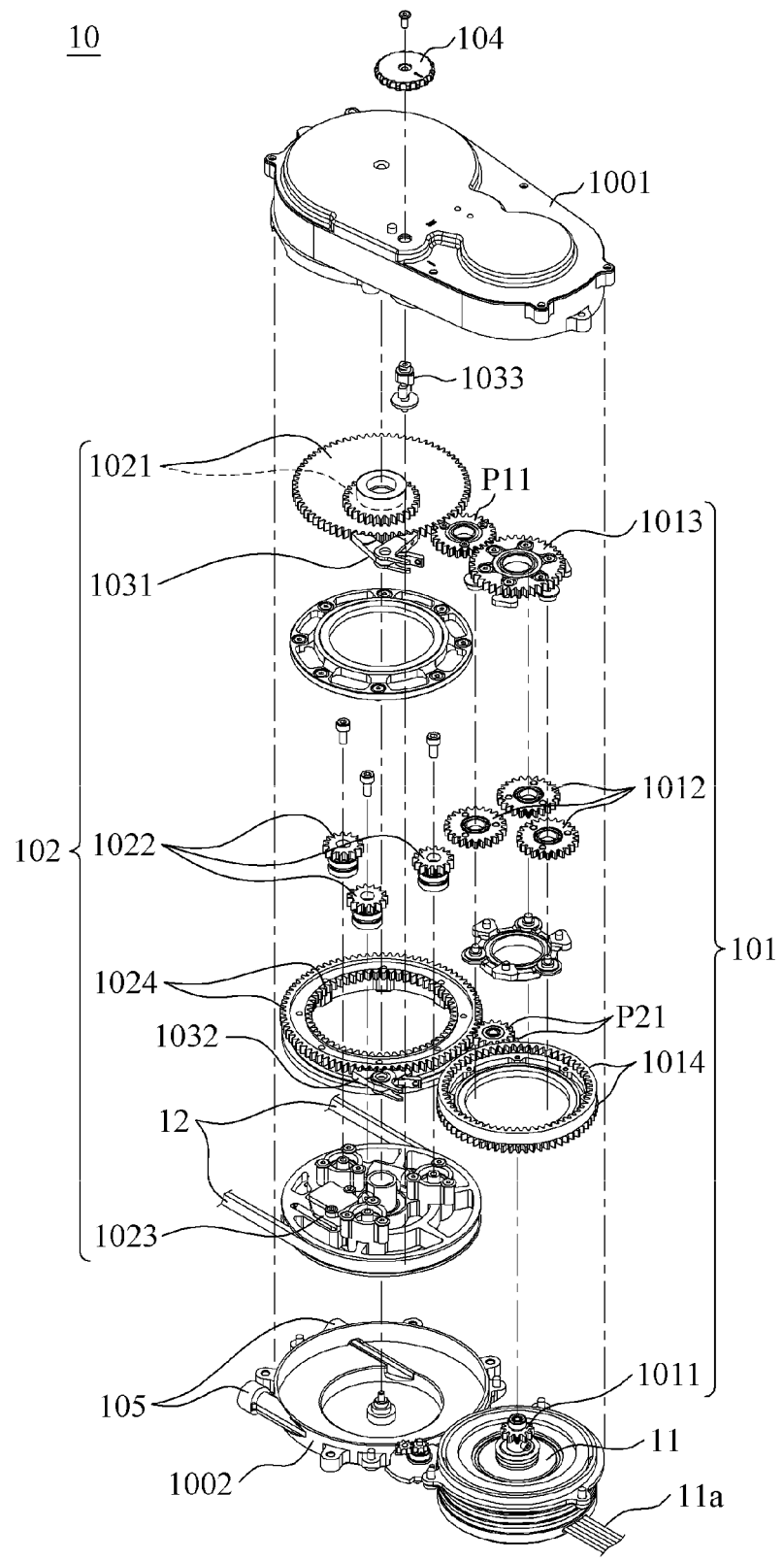
FIG. 6 is an exploded perspective view illustrating a power transmitting device according to at least one example embodiment.

FIG. 2 is a block diagram illustrating a power transmitting device according to at least one example embodiment, FIG. 3 is a diagram illustrating the power transmitting device according to at least one example embodiment, FIG. 4 is a perspective view illustrating the power transmitting device according to at least one example embodiment, FIG. 5 is a perspective view illustrating an internal structure of the power transmitting device according to at least one example embodiment, and FIG. 6 is an exploded perspective view illustrating the power transmitting device according to at least one example embodiment.

Referring to FIGS. 2 through 6, the power transmitting device 10 may transmit, to the power transmitting member 12, power received from the driving source 11. The power transmitting device 10 may include a case 100, the input side gear assembly 101, the output side gear assembly 102, a first connecting body P11, a second connecting body P21, the stopper module 103, an operator 104, and a power transmitting member guide 105.

The case 100 may be configured to hold the input side gear assembly 101, the output side gear assembly 102, the stopper module 103, the first connecting body P11, and the second connecting body P21. The case 100 may include an upper case 1001 and a lower case 1002 that form an appearance of the power transmitting device 10.

For example, the driving source 11 configured to transmit power to the power transmitting device 10 may be disposed in the case 100. For example, as shown in FIG. 6, the driving source 11 such as a motor may be disposed on one side of the lower case 1002, and a power input line 11a configured to supply power to the driving source 11 may penetrate through the lower case 1002 and be connected to the driving source 11.

The input side gear assembly 101 may have a planetary gear structure including an input side sun gear 1011, an input side planetary gear 1012, an input side carrier 1013, and an input side ring gear 1014.

The input side sun gear 1011 may function as the power input terminal of the input side gear assembly 101. The input side sun gear 1011 may receive power from the driving source 11 and transmit the power to the input side planetary gear 1012. The input side sun gear 1011 may be disposed at a center of the planetary gear structure, and connected to, for example, a rotation shaft of the driving source 11. Meanwhile, FIG. 6 illustrates a case in which the driving source 11 is disclosed in the case 100. However, unlike FIG. 6, in a case in which the driving source 11 is disposed outside of the case 100, the input side sun gear 1011 may be connected to another rotary body connected to the driving source 11, and connected indirectly to the driving source 11 to receive power from the driving source 11.

The input side planetary gear 1012 may engage with an outer circumferential surface of the input side sun gear 1011 and an inner circumferential surface of the input side ring gear 1014. The input side planetary gear 1012 may be connected to the outer circumferential surface of the input side sun gear 1011, thereby performing a rotation or revolution using power received from the input side sun gear 1011. In this example, the "revolution" may be performed about a center of rotation of the input side sun gear 1011. For a stable operation of the power transmitting device 10, a plurality of input side planetary gears 1012 may be disposed to be spaced apart from each other by the same angle in a radial form about the center of rotation of the input side sun gear 1011. FIG. 6 illustrates a state in which a total of three input side planetary gears 1012 are disposed to be spaced apart from each other at an interval of 120 degrees.

The input side carrier 1013 may be connected to a rotation axis of the input side planetary gear 1012, and rotate about the center of rotation of the input side sun gear 1011. The input side carrier 1013 may rotate at a revolution velocity of the input side planetary gear 1012. That is, the input side carrier 1013 rotates in response to the input side planetary gear 1012 performing a revolution motion. The input side carrier 1013 may include a structure to transmit power to the output side sun gear 1021, for example, external teeth formed along an outer circumferential surface thereof. Meanwhile, FIG. 6 illustrates a case in which the input side carrier 1013 is connected indirectly to the output side sun gear 1021 through the gear-shaped first connecting body P11. However, unlike FIG. 6, the first connecting body P11 may be a power transmitting member provided in another shape, for example, a timing belt connecting the input side carrier 1013 and the output side sun gear 1021. The input side carrier 1013 may also be connected directly to the output side sun gear 1021, without using the first connecting body P11.

The first connecting body P11 may be, for example, an idle gear configured to transmit a rotation motion of the input side carrier 1013 intactly to the output side sun gear 1021, as shown in FIG. 6. In another example, the first connecting body P11 may be a compound gear including two sets of external teeth having different diameters, the sets of the external teeth configured to engage with the input side carrier 1013 and the output side sun gear 1021, respectively. In this example, the first connecting body P11 may change a speed of the rotation motion of the input side carrier 1013 and transmit the speed-changed rotation motion to the output side sun gear 1021.

The input side ring gear 1014 may be a ring-shaped gear configured to enclose an outer side of the input side planetary gear 1012, and include an inner circumferential surface on which internal teeth are formed to engage with the teeth formed on the outer circumferential surface of the input side planetary gear 1012. In addition to the internal teeth, the input side ring gear 1014 may also include a structure to transmit power to the output side ring gear 1024, for example, external teeth formed along an outer circumferential surface thereof. Meanwhile, FIG. 6 illustrates a case in which the input side ring gear 1014 is connected indirectly to the output side ring gear 1024 through the gear-shaped second connecting body P21. However, unlike FIG. 6, the second connecting body P21 may be a power transmitting member provided in another shape, for example, a timing belt connecting the input side ring gear 1014 and the output side ring gear 1024. The input side ring gear 1014 may be connected directly to the output side ring gear 1024, without using the second connecting body P21.

The second connecting body P21 may be, for example, a compound gear including two sets of external teeth having different diameters, the sets of the external teeth configured to engage with the input side ring gear 1014 and the output side ring gear 1024, respectively, as shown in FIG. 6. In this example, the second connecting body P21 may change a speed of a rotation motion of the input side ring gear 1014 and transmit the speed-changed rotation motion to the output side ring gear 1024. In another example, the second connecting body P21 may be an idle gear configured to transmit the rotation motion intactly to the output side sun gear 1021.

The revolution motion of the input side planetary gear 1012 may rotate the input side carrier 1013, and a rotation motion of the input side planetary gear 1012 may rotate the input side ring gear 1014. Thus, the input side carrier 1013 and the input side ring gear 1014 may function as the two power output terminals of the input side gear assembly 101.

The output side gear assembly 102 may have a planetary gear structure including an output side sun gear 1021, an output side planetary gear 1022, an output side carrier 1023, and an output side ring gear 1024. Unless otherwise mentioned, the description about the configuration of the input side gear assembly 101 may apply to the configuration of the output side gear assembly 102. Thus, duplicated descriptions will be omitted for conciseness.

The output side sun gear 1021 and the output side ring gear 1024 may function as the power input terminals of the output side gear assembly 102. The output side sun gear 1021 and the output side ring gear 1024 may be connected to the input side carrier 1013 and the input side ring gear 1014, respectively, and transmit power to the output side planetary gear 1022.

The output side sun gear 1021 may function as one of the plurality of power input terminals of the output side gear assembly 102. The output side sun gear 1021 may receive power from the input side gear assembly 101 and transmit the power to the output side planetary gear 1022. The output side sun gear 1021 may be disposed at a center of revolution of at least one output side planetary gear 1022. For example, the output side sun gear 1021 may be provided in a form of a compound gear having first external teeth configured to operate using power received from the input side carrier 1013 and second external teeth configured to engage with the output side planetary gear 1022, the second external teeth having a smaller diameter than the first external teeth.

Similar to the output side sun gear 1021, the output side ring gear 1024 may function as one of the plurality of power input terminals of the output side gear assembly 102. The output side ring gear 1024 may receive power from the input side ring gear 1014 and transmit the power to the output side planetary gear 1022. In addition to the internal teeth engaging with the output side planetary gear 1022, the output side ring gear 1024 may include a structure to operate using the power received from the input side ring gear 1014, for example, external teeth formed on an outer circumferential surface thereof.

The output side planetary gear 1022 may engage with the output side sun gear 1021 and the output side ring gear 1024. The output side planetary gear 1022 may perform a rotation or revolution using power received from the output side sun gear 1021 or the output side ring gear 1024. In this example, the "revolution" may be performed about a center of rotation of the output side sun gear 1021.

The output side carrier 1023 may be connected to a rotation axis of the output side planetary gear 1022, and rotate about the center of rotation of the output side sun gear 1021. The output side carrier 1023 may rotate at a revolution velocity of the output side planetary gear 1022. Thus, the output side carrier 1023 may function as the single power output terminal of the output side gear assembly 102.

As described above, the power transmitting device 10 may include the two power transmitting paths P1 and P2 that receive power from the driving source 11 and transmit the power to the power transmitting member 12.

The first power transmitting path P1 may be a power transmitting path that sequentially connects the driving source 11, the input side sun gear 1011, the input side planetary gear 1012, the input side carrier 1013, the output side sun gear 1021, the output side planetary gear 1022, the output side carrier 1023, and the power transmitting member 12.

The second power transmitting path P2 may be a power transmitting path that sequentially connects the driving source 11, the input side sun gear 1011, the input side planetary gear 1012, the input side ring gear 1014, the output side ring gear 1024, the output side planetary gear 1022, the output side carrier 1023, and the power transmitting member 12.

In the above configuration, due to a planetary gear structure, the first power transmitting path P1 may have a high reduction ratio when compared to the second power transmitting path P2.

The stopper module 103 may include a first stopper 1031 configured to block power to be transmitted through the first power transmitting path P1, a second stopper 1032 configured to block power to be transmitted through the second power transmitting path P2, and a cam module 1033 configured to change states of the first stopper 1031 and/or the second stopper 1032.

The first stopper 1031 may engage with one of components not shared with the second power transmitting path P2, among the plurality of components included in the first power transmitting path P1, for example, the input side carrier 1013, the first connecting body P11, and the output side sun gear 1021, thereby blocking power to be transmitted through the first power transmitting path P1. The input side carrier 1013, the first connecting body P11, and the output side sun gear 1021 may be collectively referred to as "first power transmitting elements". For example, in response to the input side carrier 1013 being fixed as the first stopper 1031 operates, the input side planetary gear 1012 may not perform a revolution any more, but perform a rotation. Thus, the power transmitted to the input side planetary gear 1012 may be used to rotate the input side ring gear 1014 and the components connected to the input side ring gear 1014. Therefore, the first stopper 1031 may be construed as transmitting power through the second power transmitting path P2.

The second stopper 1032 may engage with one of components not shared with the first power transmitting path P1, among the plurality of components included in the second power transmitting path P2, for example, the input side ring gear 1014, the second connecting body P21, and the output side ring gear 1024, thereby blocking power to be transmitted through the second power transmitting path P2. The input side ring gear 1014, the second connecting body P21, and the output side ring gear 1024 may be collectively referred to as "second power transmitting elements". For example, in response to the input side sun gear 1011 rotating in a state in which the input side ring gear 1014 is fixed as the second stopper 1032 operates, the input side planetary gear 1012 may perform a revolution and a rotation simultaneously. Thus, the power transmitted to the input side planetary gear 1012 may be used to rotate the input side carrier 1013 and the components connected to the input side carrier 1013. Therefore, the second stopper 1032 may be construed as transmitting power through the first power transmitting path P1.

Based on a rotation angle of the cam module 1033, the first stopper 1031 and the second stopper 1032 may prevent rotations of the first power transmitting elements and the second power transmitting elements, respectively.

The operator 104 may be rotatably disposed on the upper case 1001, and connected to the cam module 1033. A user may control the operator 104 exposed outside of the upper case 1001 to change the rotation angle of the cam module 1033 disposed in the case 100. The operator 104 may be controlled manually by the user, or controlled automatically through a controller configured to control the power transmitting device 10. In other example embodiments, the controller may control the cam module 1033 instead of the operator 104.

The controller may control the operator 104 or the cam module 1033 by sending a signal to an actuator (not shown) attached to the operator 104 or the cam module 1033 to instruct the actuator to rotate the same.

Figure 7:
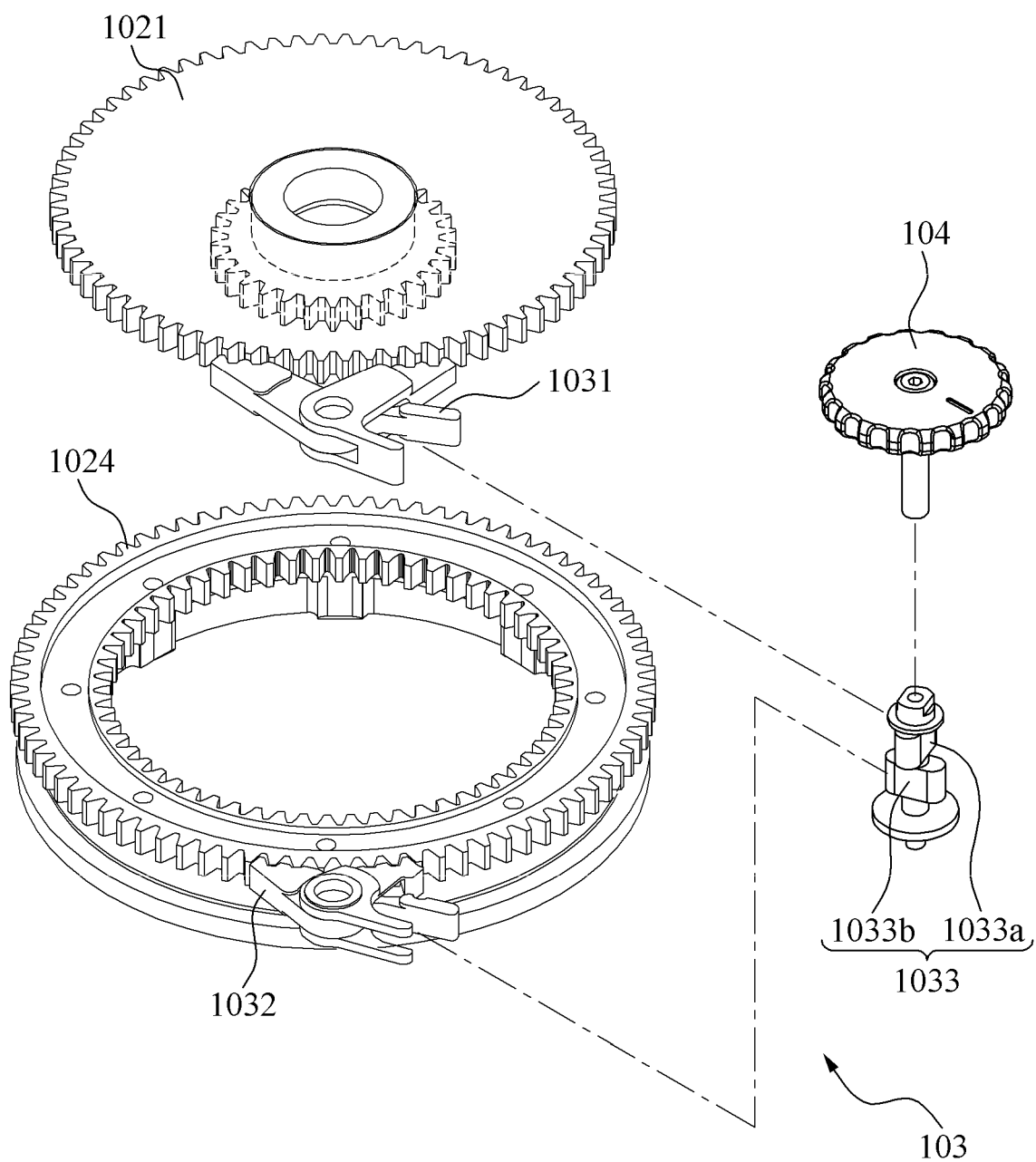
FIG. 7 is an exploded perspective view illustrating a state of a stopper module when a power transmitting device transmits power through a first power transmitting path according to at least one example embodiment.
Figure 8:
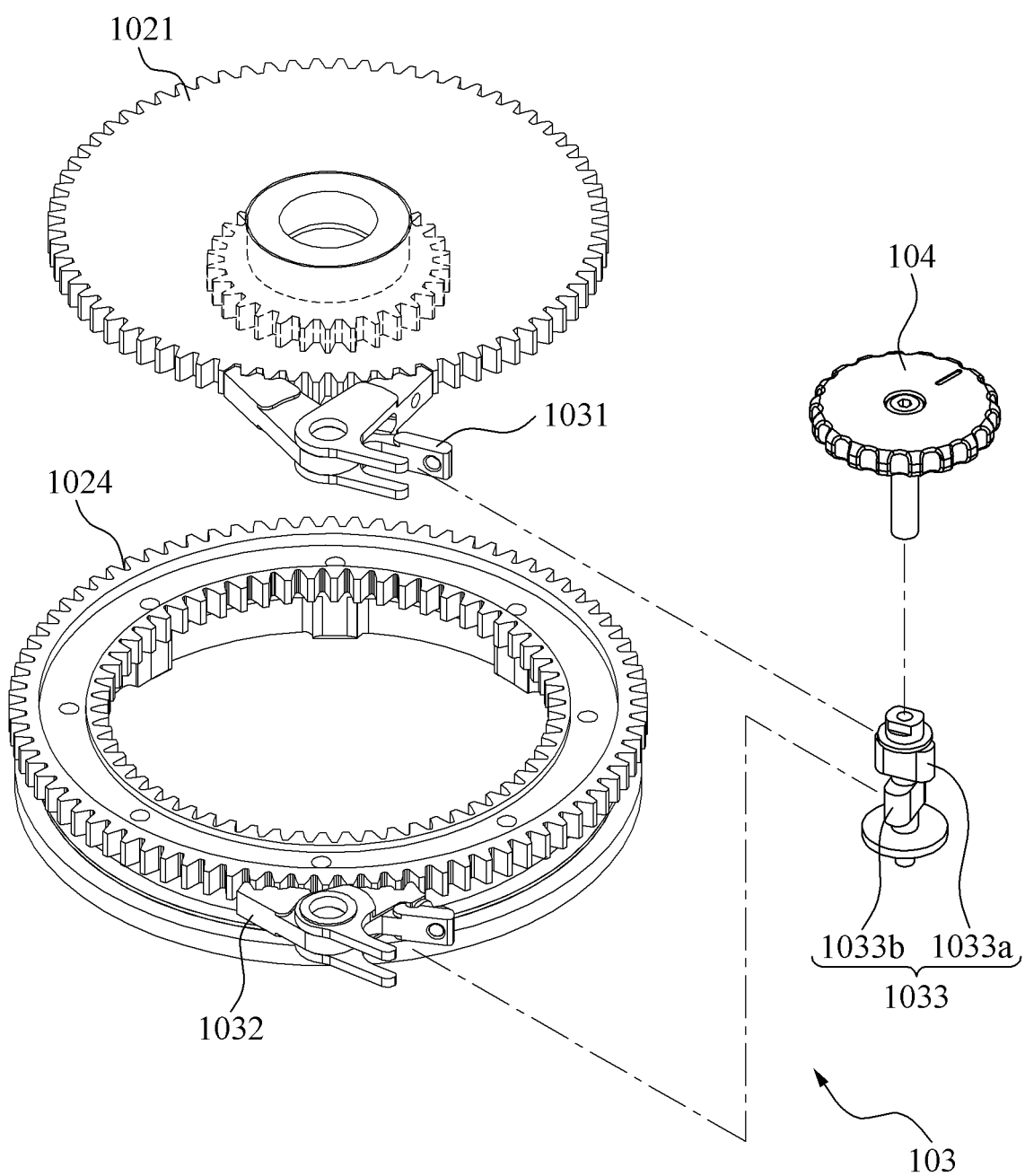
FIG. 8 is an exploded perspective view illustrating a state of a stopper module when a power transmitting device transmits power through a second power transmitting path according to at least one example embodiment.

Further, while FIGS. 6-8 describe an example embodiment in which the cam module 1033 rotates such that the first stopper 1031 and the second stopper 1032 selectively engage with a respective one of the first power transmitting elements and the second power transmitting elements to block power transmission, example embodiments are not limited thereto.

For example, in other example embodiments, the cam module 1033 may be connected to the first connecting body P11 and the second connecting body P21 and may selectively disengage one of the connecting bodies P11, P21 to stop power transmission rather than engage with one of the first power transmitting elements and the second power transmitting elements. Therefore, since the first power transmitting elements and the second power transmitting elements are allowed to freely spin, less heat may be generated, and thus, power consumption may decrease.

FIG. 7 is an exploded perspective view illustrating a state of a stopper module when a power transmitting device transmits power through a first power transmitting path according to at least one example embodiment, and FIG. 8 is an exploded perspective view illustrating a state of the stopper module when the power transmitting device transmits power through a second power transmitting path according to at least one example embodiment.

Referring to FIGS. 7 and 8, the first stopper 1031 may operate in a "restraint state" to engage with at least one of the plurality of first power transmitting elements disposed on the first power transmitting path P1, for example, the input side carrier 1013, the first connecting body P11, and the output side sun gear 1021, or in a "release state" not to engage with any of the plurality of first power transmitting elements.

For example, the first stopper 1031 may include a pair of pincers configured to rotate about a single center of rotation, and a pair of extensions extending from the pair of pincers, respectively. The extensions may extend in directions different from directions in which the pincers protrude, respectively, based on the single center of rotation. That is, the first stopper 1031 may have a shape similar to scissors. In the above structure, as a distance between the pair of extensions decreases, a distance between the pair of pincers may also decrease. In this example, the pair of pincers may engage with the output side sun gear 1021, whereby the first stopper 1031 may be in the "restraint state". Conversely, as the distance between the pair of extensions increases, the distance between the pair of pincers may also increase. In this example, the pair of pincers may be disengaged from the output side sun gear 1021, whereby the first stopper 1031 may be in the "release state".

The first stopper 1031 may further include an elastic member configured to provide an elastic force to rotate the pair of pincers in opposite directions. For example, the elastic member may be a torsion spring that decreases the distance between the pair of pincers while an external force is not applied to the first stopper 1031.

Similarly, the second stopper 1032 may operate in a "restraint state" to engage with at least one of the plurality of second power transmitting elements disposed on the second power transmitting path P2, for example, the input side ring gear 1014, the second connecting body P21, and the output side ring gear 1024, or in a "release state" not to engage with any of the plurality of second power transmitting elements. Unless otherwise mentioned, the description of the first stopper 1031 may apply to the second stopper 1032, and thus duplicated descriptions will be omitted for conciseness.

The cam module 1033 may include a first cam 1033*a* configured to switch the state of the first stopper 1031, and a second cam 1033*b* configured to switch the state of the second stopper 1032.

The first cam 1033*a* may be disposed between the pair of extensions of the first stopper 1031, and the second cam 1033*b* may be disposed between the pair of extensions of the second stopper 1032. The first cam 1033*a* and the second cam 1033*b* may intersect each other, and perform a single rigid body motion. In the above structure, the state of the first stopper 1031 may be the opposite of the state of the second stopper 1032. In detail, in response to the first stopper 1031 being in the restraint state, the second stopper 1032 may be in the release state. In response to the first stopper 1031 being in the release state, the second stopper 1032 may be in the restraint state. For example, in response to the first cam 1033*a* and the second cam 1033*b* being orthogonal to each other, the states of the first stopper 1031 and the second stopper 1032 may change each time the rotation angle of the cam module 1033 changes at an interval of 90 degrees.

Figure 9:
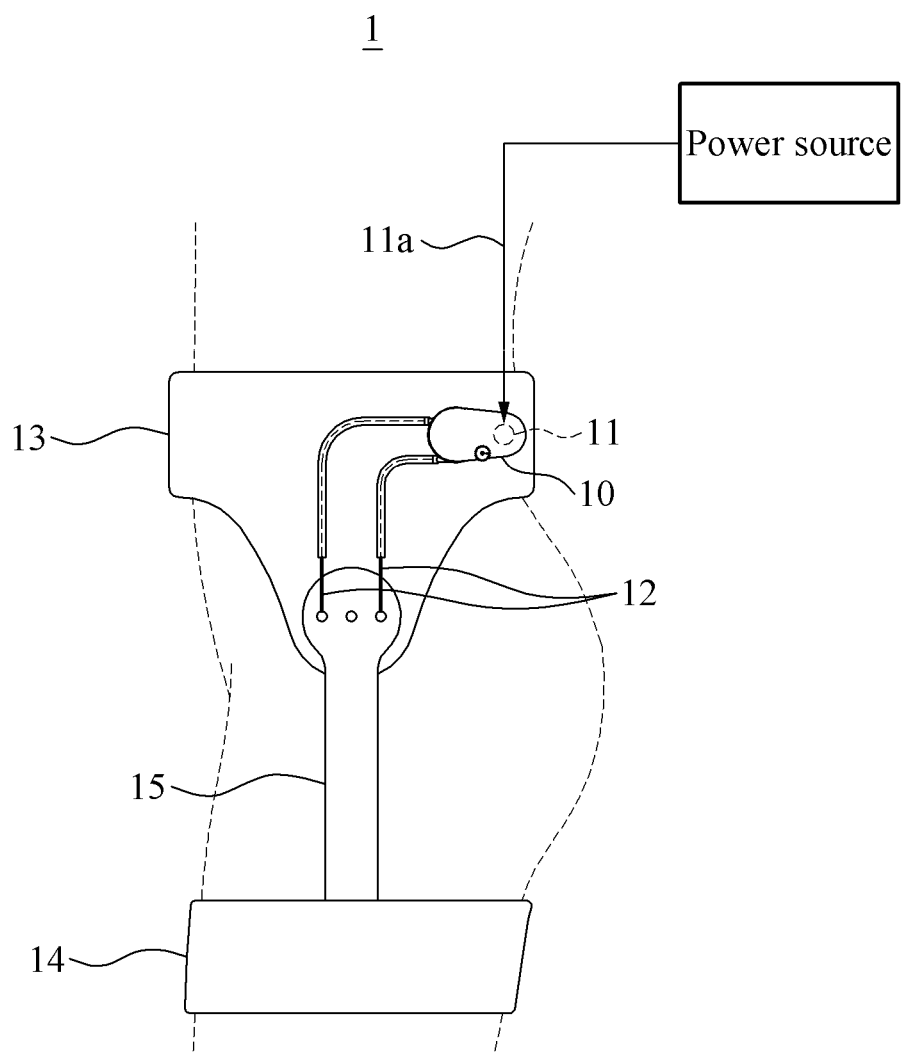
FIG. 9 is a view illustrating a motion assistance apparatus including a power transmitting device according to at least one example embodiment.

FIG. 9 is a view illustrating a motion assistance apparatus including a power transmitting device according to at least one example embodiment.

Referring to FIG. 9, a motion assistance apparatus 1 may be worn by a user to assist a motion of the user. The user may correspond to a human, an animal, or a robot. However, the user is not limited thereto. Although FIG. 9 illustrates a case in which the motion assistance apparatus 1 assists a motion of a hip joint of the user, the motion assistance apparatus 1 may also assist a motion of another portion in an upper body, for example, a wrist, an elbow, or a shoulder of the user, or a motion of another portion in a lower body, for example, an ankle or a knee of the user. The motion assistance apparatus 1 may assist a motion of a portion of the user. Hereinafter, a case in which the motion assistance apparatus 1 assists a motion of a hip joint of a human will be described. However, example embodiments are not limited thereto.

The motion assistance apparatus 1 may include the driving source 11 configured to generate power, the power input line 11*a* configured to supply power from a power source to the driving source 11, the power transmitting device 10 connected to the driving source 11, a first supporting member 13 configured to support a first portion of the user, for example, a waist, a second supporting member 14 configured to support a second portion of the user, for example, a thigh, a power transmitting frame 15 connected to the second supporting member 14 and configured to rotate relative to the first supporting member 13, and the power transmitting member 12 configured to transmit power from the power transmitting device 10 to the power transmitting frame 15.

In some example embodiments, the driving source 11 may be disposed in the case of the power transmitting device 10, as shown in FIG. 9. However, example embodiments are not limited thereto.

The power transmitting device 10 may receive the power generated by the driving source 11 and transmit the power to the power transmitting frame 15 through the power transmitting member 12, thereby rotating the power transmitting frame 15 relative to the first supporting member 13. The power transmitting member 12 may be, for example, a cable or a belt.

The power transmitting device 10 may be fixed to the first supporting member 13. The power transmitting device 10 may be disposed on the first supporting member 13 at a position corresponding to gluteus minimus muscle of the user which is a back side of the waist of the user. The gluteus minimus muscle corresponds to a space dimpled when compared to another portion of a human. The above disposition may prevent external protrusion of the power transmitting device 10. Thus, the entire volume of the motion assistance apparatus 1 may look small externally, and an arm of the user may move in freedom.

Figure 10:
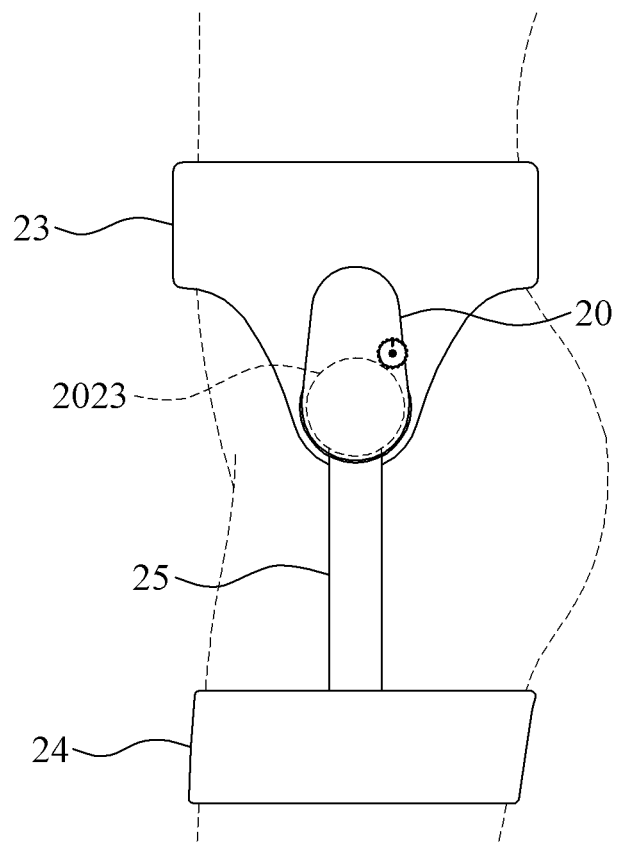
FIG. 10 is a view illustrating a motion assistance apparatus including a power transmitting device according to at least one example embodiment.

FIG. 10 is a view illustrating a motion assistance apparatus including a power transmitting device according to at least one example embodiment.

Referring to FIG. 10, a motion assistance apparatus 2 may include a power transmitting device 20, a first supporting member 23, a second supporting member 24, and a power transmitting frame 25.

The power transmitting device 20 may be connected directly to the power transmitting frame 25 to transmit power to the power transmitting frame 25, without using a separate power transmitting member. For example, as shown in FIG. 10, an output side carrier 2023 configured to function as a final output terminal of the power transmitting device 20 may be connected directly to the power transmitting frame 25. In this example, the output side carrier 2023 may be disposed on a joint positioned between the first supporting member 23 and the second supporting member 24, for example, a hip joint.

Figure 11:
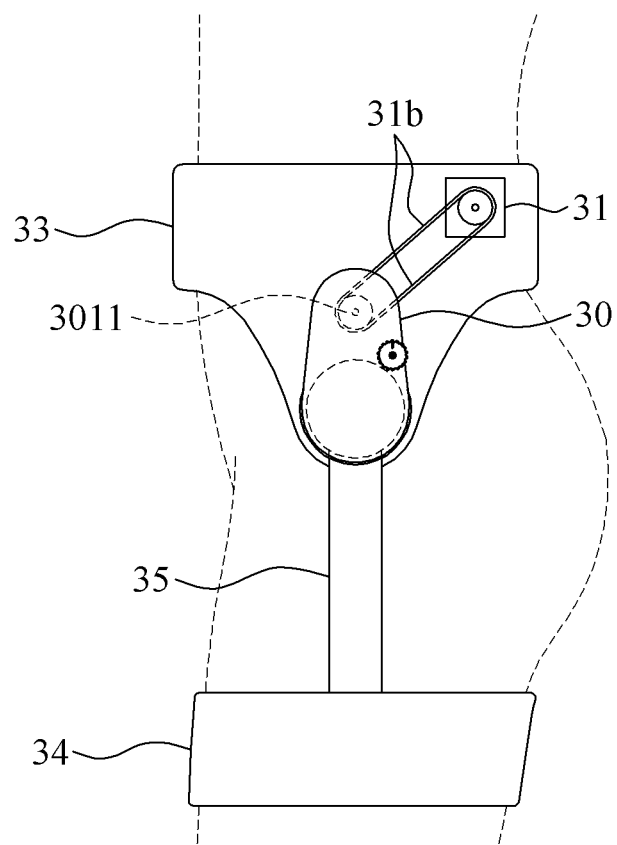
FIG. 11 is a view illustrating a motion assistance apparatus including a power transmitting device according to at least one example embodiment.

FIG. 11 is a view illustrating a motion assistance apparatus including a power transmitting device according to at least one example embodiment.

Referring to FIG. 11, a motion assistance apparatus 3 may include a driving source 31, a power transmitting line 31b, a power transmitting device 30, a first supporting member 33, a second supporting member 34, and a power transmitting frame 35.

The driving source 31 may be disposed outside of a case of the power transmitting device 30, as shown in FIG. 11. The power transmitting line 31b may transmit power generated by the driving source 31 to an input side sun gear 3011 of the power transmitting device 30. The power transmitting line 31b may be, for example, a flexible cable or belt, and the input side sun gear 3011 may correspond to the input side sun gear 1011.

The driving source 31 may be fixed to the first supporting member 33. The driving source 31 may be disposed on the first supporting member 33 at a position corresponding to gluteus minimus muscle of the user. The above disposition may prevent external protrusion of the driving source 31. Thus, the entire volume of the motion assistance apparatus 3 may look small externally, and an arm of the user may move in freedom.

Figure 12:
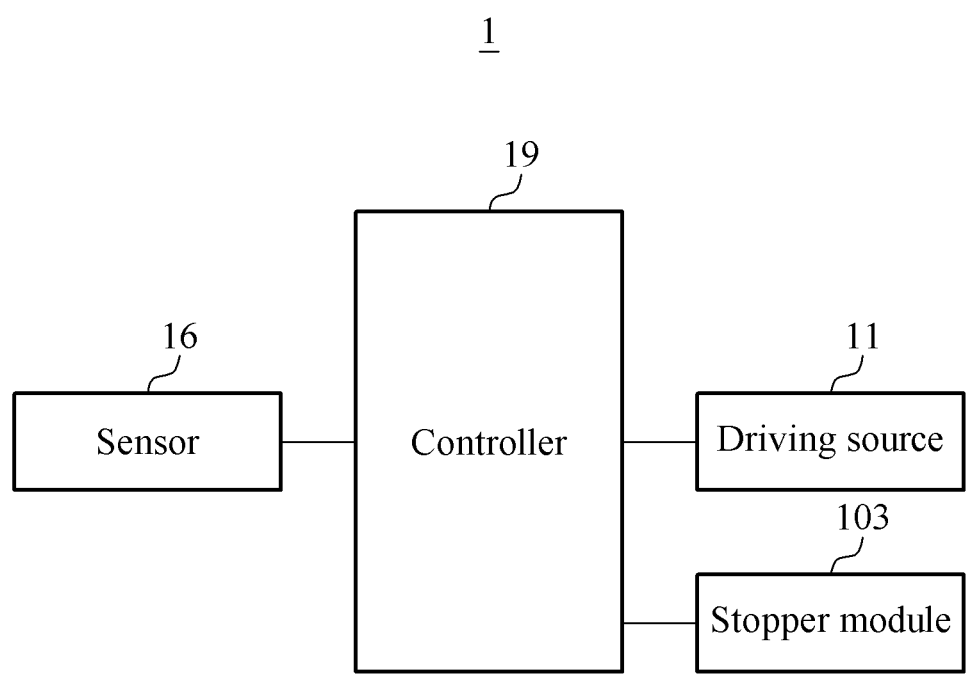
FIG. 12 is a block diagram illustrating a motion assistance apparatus including a power transmitting device according to at least one example embodiment.

FIG. 12 is a block diagram illustrating a motion assistance apparatus including a power transmitting device according to at least one example embodiment, and FIGS. 13 through 16 are flowcharts illustrating methods of controlling the motion assistance apparatus including the power transmitting device according to at least one example embodiment.

Referring to FIG. 12, the motion assistance apparatus 1 may include the power transmitting device 10 including the stopper module 103, the driving source 11, a sensor 16 configured to sense information related to a motion of a user, hereinafter, motion information of the user, and a controller 19 configured to control the driving source 11 and the stopper module 103 based on the motion information sensed by the sensor 16.

The controller 19 may include a processor and a memory (not shown).

The processor may be a data processing device implemented as hardware including a circuit having a physical structure for executing desired operations included in a computer readable code stored in the memory. For example, the processor may include a microprocessor, a central processing unit (CPU), a processor core, a multi-core processor, a multiprocessor, an application-specific integrated circuit (ASIC), and a field programmable gate array (FPGA).

The memory may be a nonvolatile memory device, a volatile memory device, a non-transitory storage medium, or a combination of two or more of the above-mentioned devices. For example, the memory may include Read Only Memory (ROM), Random Access Memory (RAM), Compact Disk-Read Only Memories (CD-ROMs), magnetic tapes, floppy disks, and an optical recording medium.

As discussed in more detail below, the computer readable code may configure the processor as a special purpose computer to perform the operations illustrated in one or more of FIGS. 13-16 such that the processor is configured to determine one or more of a motion task being performed by the user and a desired torque level associated therewith based on motion information connected by the sensor 16, and to adjust an assistance force provided by the motion assistance apparatus 1 by controlling the cam 1033 to move to one of a first position and a second position based on the one or more of the motion task and the desired torque level.

Figure 13:
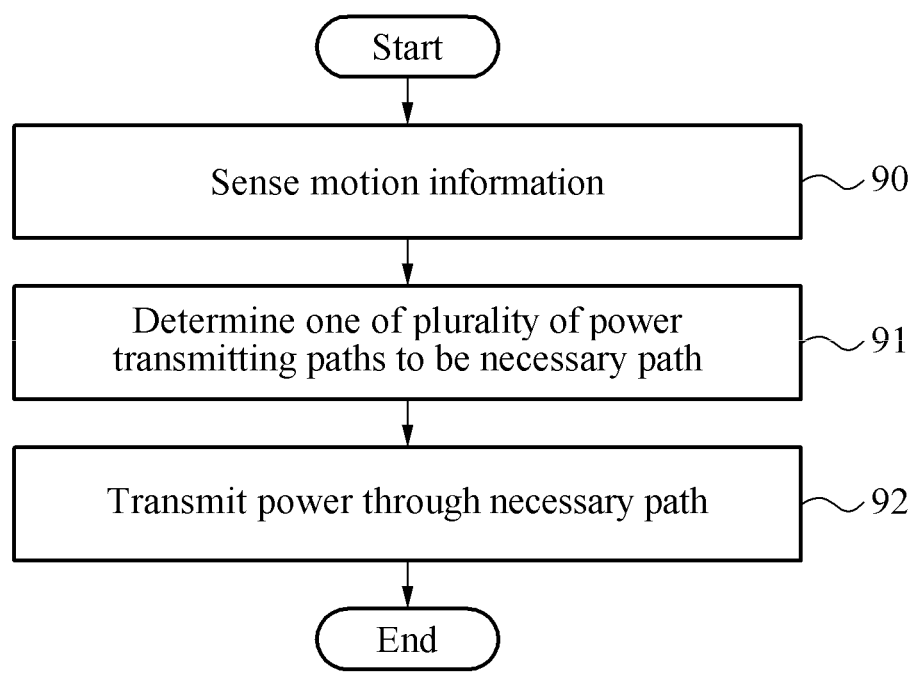
FIGS. 13 through 16 are flowcharts illustrating methods of controlling a motion assistance apparatus including a power transmitting device according to at least one example embodiment.

Referring to FIG. 13, a method of controlling a motion assistance apparatus may include operation 90 of sensing motion information of a user, operation 91 of determining one of a plurality of power transmitting paths to be a necessary path, and operation 92 of transmitting power through the necessary path.

In operation 90, the sensor 16 may sense the motion information of the user and transmit the motion information to the controller 19. The sensor 16 may be any sensor configured to sense the motion information of the user. The motion information may include, for example, a force, pressure, or torque applied to a body of the user or a component constituting the motion assistance apparatus 1, an angle between the body of the user or the component constituting the motion assistance apparatus 1 and the ground, a speed or acceleration of the body of the user or the component constituting the motion assistance apparatus 1, a rotation angle, angular velocity, or angular acceleration of a joint of the user or the motion assistance apparatus 1. The sensor 16 may include, for example, at least one of a force sensor, a pressure sensor, a torque sensor, a strain gauge, an electromyography (EMG) sensor, an inertial measurement unit (IMU), an encoder, an accelerometer, or a gyroscope to be attached to the body of the user or the component constituting the motion assistance apparatus 1.

In operation 91, the controller 19 may determine one of the plurality of power transmitting paths included in the power transmitting device to be the desired power transmitting path based on the motion information sensed by the sensor 16. For example, the controller 19 may determine which of the first power transmitting path P1 and the second power transmitting path P2 is the desired power transmitting path based on the motion information.

In operation 92, the controller 19 may control the stopper module 103 to enable the power transmitting device to transmit power through the desired power transmitting path.

Figure 14:
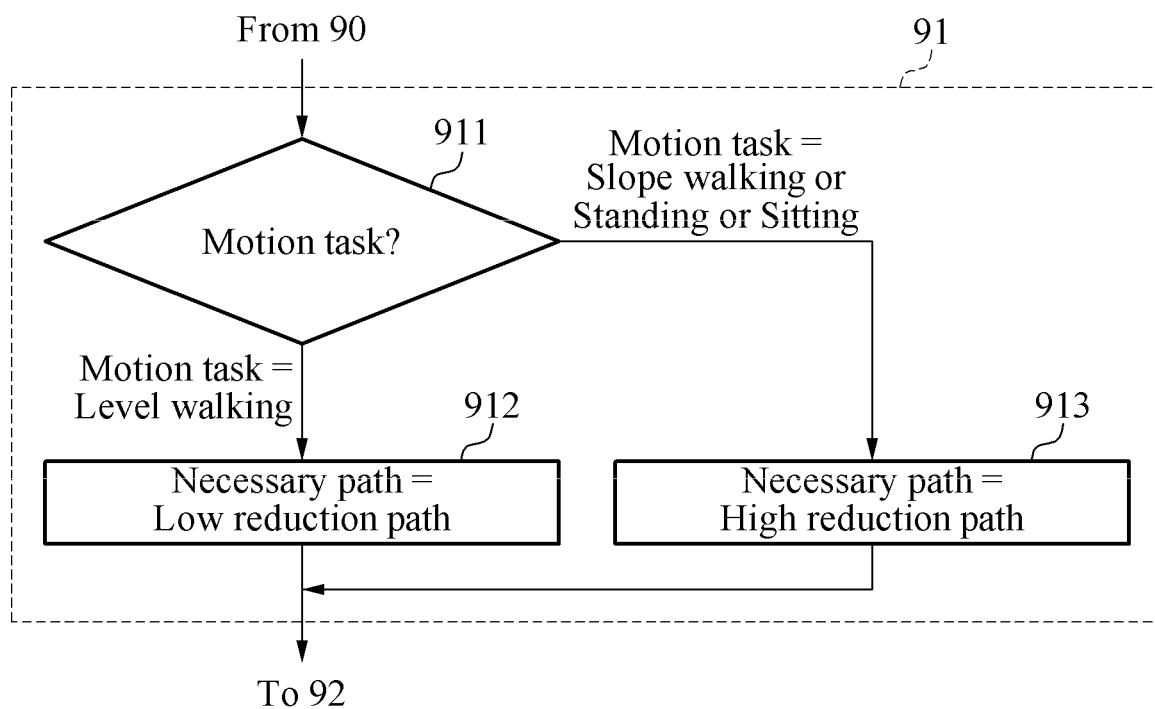

Referring to FIGS. 13 and 14, in some example embodiments, operation 91 of FIG. 13 may include operation 911 of determining a motion task of the user, and operations 912 and 913 of determining a necessary path based on the determined motion task.

In operation 911, the controller 19 may determine the motion task of the user based on the motion information sensed by the sensor 16. For example, the sensor 16 may include an IMU attached to a leg of the user. In response to a pattern of a value measured by the sensor 16 being similar to a provided pattern corresponding to level walking, the controller 19 may determine the motion task of the user to correspond to level walking. However, operation 911 is not limited to thereto.

In operation 912, in response to the determined motion task corresponding to a task requiring a relatively fast speed rather than a relatively great torque, like level walking, the controller 19 may determine the desired power transmitting path of the power transmitting device to be a power transmitting path with a low reduction ratio, for example, the second power transmitting path P2.

In operation 913, in response to the determined motion task corresponding to a task requiring a relatively great torque rather than a relatively fast speed, like slope walking, standing, or sitting, the controller 19 may determine the necessary path of the power transmitting device to be a power transmitting path with a high reduction ratio, for example, the first power transmitting path P1.

Figure 15:
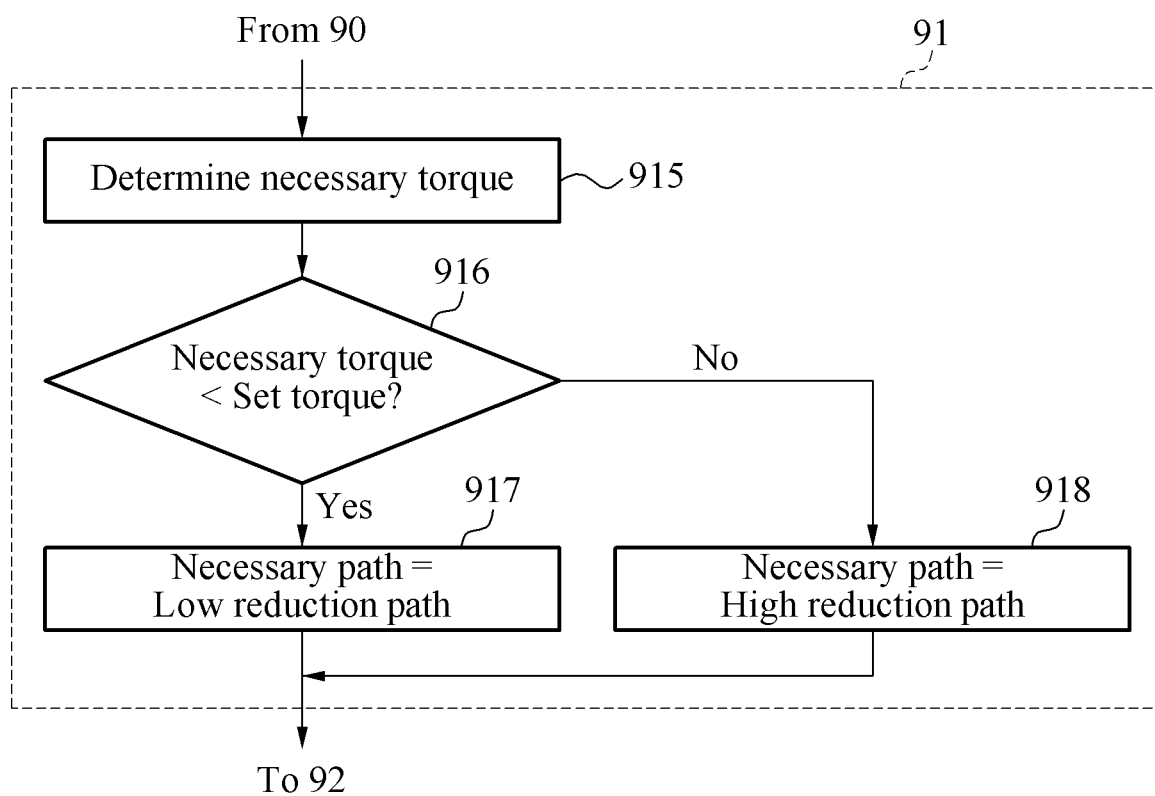

Referring to FIGS. 13 and 15, in other example embodiments, operation 91 of FIG. 13 may include operation 915 of determining a necessary torque to be provided to the user, operation 916 of determining whether the determined necessary torque is less than a set torque, and operations 917 and 918 of determining a desired power transmitting path based on a result of operation 916.

In operation 915, the controller 19 may determine the necessary torque based on the motion information sensed by the sensor 16. For example, the sensor 16 may include a pressure sensor disposed between a supporting member of the motion assistance apparatus 1 and a body of the user. The controller 19 may determine the necessary torque to be a value proportional to a pressure sensed by the sensor 16. In another example, the controller 19 may determine a motion task of the user based on the motion information sensed by the sensor 16, and determine the necessary torque based on the determined motion task. However, operation 915 is not limited thereto.

In operation 917, in response to the determined necessary torque being less than the set torque, the controller 19 may determine the desired power transmitting path of the power transmitting device to be a power transmitting path with a low reduction ratio, for example, the second power transmitting path P2.

In operation 918, in response to the determined necessary torque being greater than or equal to the set torque, the controller 19 may determine the desired power transmitting path of the power transmitting device to be a power transmitting path with a high reduction ratio, for example, the first power transmitting path P1.

Figure 16:
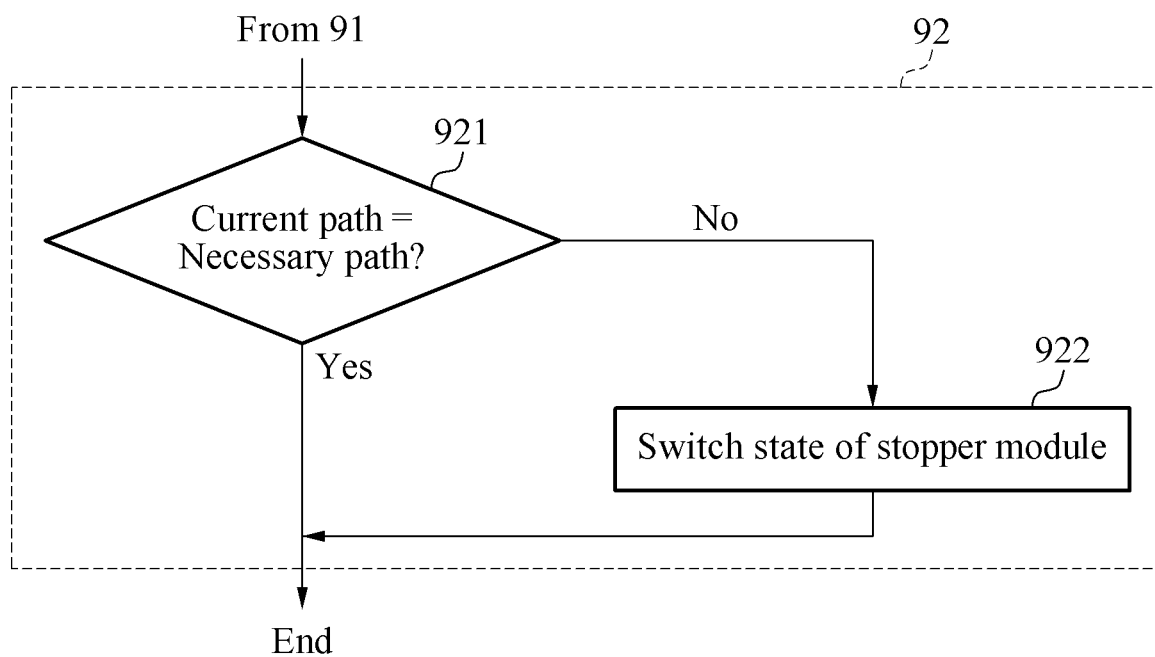

Referring to FIG. 16, operation 92 of FIG. 13 may include operation 921 of determining whether a current path of the power transmitting device matches the necessary path, and operation 922 of switching a state of a stopper module based on a result of operation 921.

In operation 921, the controller 19 may determine a power transmitting path corresponding to the current path through which the power transmitting device is currently transmitting power, based on a state of the stopper module 103, for example, a rotation angle of the cam module 1033 of the stopper module 103. In response to the current path not matching the desired power transmitting path, the controller 19 may switch the state of the stopper module 103 by rotating the cam module 1033 such that the power transmitting path of the power transmitting device may be the same as the desired power transmitting path.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A power transmitting device comprising:
   an input side gear assembly including a first power input terminal and a plurality of first power output terminals;
   an output side gear assembly including a plurality of second power input terminals and a second power output terminal, the plurality of second power input terminals configured to receive power from the plurality of first power output terminals of the input side gear assembly, respectively; and
   a stopper mechanism configured to select, for power transmission, one of a plurality of power transmitting paths connecting the plurality of first power output terminals and the plurality of second power input terminals, the stopper mechanism including a cam mechanism configured to rotate at least among a first position and a second position, the first position being a position in which the stopper mechanism engages with a first one of the plurality of second power input terminals and disengages from a second one of the plurality of second power input terminals, and the second position being a position in which the stopper mechanism is disengaged from the first one of the plurality of second power input terminals and engages with the second one of the plurality of second power input terminals.

2. The power transmitting device of claim 1, wherein the input side gear assembly comprises:
   an input side sun gear, the input side sun gear being the first power input terminal;
   an input side planetary gear connected to an outer circumferential surface of the input side sun gear, the input side planetary gear configured to rotate based on power received from the input side sun gear; and an input side carrier and an input side ring gear each connected to the input side planetary gear, the input side carrier and the input side ring gear each being one of the plurality of first power output terminals.

3. The power transmitting device of claim 1, wherein the stopper mechanism comprises:
   a first stopper configured to block power transmission through a first power transmitting path of the plurality of power transmitting paths; and
   a second stopper configured to block power transmission through a second power transmitting path of the plurality of power transmitting paths.

4. The power transmitting device of claim 3, wherein the first stopper is configured to operate in one of a first restraint state and a first release state, the first restraint state being a state in which the first stopper is configured to engage with at least one of a plurality of first power transmitting elements on the first power transmitting path, and the first release state being a state in which the first stopper is disengaged from the plurality of first power transmitting elements, and
   the second stopper is configured to operate in one of a second restraint state and a second release state, second restraint state being a state in which the second stopper is configured to engage with at least one of a plurality of second power transmitting elements disposed on the second power transmitting path, and the second release state being a state in which the second stopper is disengaged from the plurality of second power transmitting elements.

5. The power transmitting device of claim 4, wherein the stopper mechanism further comprises:
   the cam mechanism configured to,
      enable the second stopper to operate in the second release state in response to the first stopper operating in the first restraint state, and
      enable the second stopper to operate in the second restraint state in response to the first stopper operating in the first release state.

6. The power transmitting device of claim 5, wherein the first stopper is configured to switch between the first restraint state and the first release state and the second stopper is configured to switch between the second restraint state and the second release state in response to the cam mechanism rotating 90 degrees.

7. The power transmitting device of claim 5, wherein the cam mechanism comprises:
   a first cam configured to switch the first stopper between the first restraint state and the first release state; and
   a second cam configured to switch the second stopper between the second restraint state and the second release state.

8. The power transmitting device of claim 7, wherein the first cam and the second cam are configured to perform a single rigid body motion.

9. The power transmitting device of claim 7, wherein the first cam and the second cam are orthogonal to each other.

10. The power transmitting device of claim 7, wherein the first stopper and the second stopper each comprise:
    a pair of pincers configured to rotate about a single center of rotation, and
    a pair of extensions extending from the pair of pincers, respectively, wherein
       the first cam is between the pair of extensions of the first stopper, and
       the second cam is between the pair of extensions of the second stopper.

11. The power transmitting device of claim 10, wherein the first stopper and the second stopper each further comprise:
    an elastic member configured to provide elastic force to rotate the pair of pincers in opposite directions.

12. A power transmitting device comprising:
    an input side gear assembly including a first power input terminal and a plurality of first power output terminals;
    an output side gear assembly including a plurality of second power input terminals and a second power output terminal, the plurality of second power input terminals configured to receive power from the plurality of first power output terminals of the input side gear assembly, respectively; and
    a stopper mechanism configured to select, for power transmission, one of a plurality of power transmitting paths connecting the plurality of first power output terminals and the plurality of second power input terminals,
    wherein the input side gear assembly includes,
       an input side sun gear, the input side sun gear being the first power input terminal;
       an input side planetary gear connected to an outer circumferential surface of the input side sun gear, the input side planetary gear configured to rotate based on power received from the input side sun gear; and
       an input side carrier and an input side ring gear each connected to the input side planetary gear, the input side carrier and the input side ring gear each being one of the plurality of first power output terminals, and
    wherein the output side gear assembly includes,
       an output side sun gear and an output side ring gear connected to the input side carrier and the input side ring gear, respectively, the output side sun gear and the output side ring gear each being one of the plurality of second power input terminals;
       an output side planetary gear configured to engage with the output side sun gear and the output side ring gear; and
       an output side carrier connected to a rotation axis of the output side planetary gear, and the output side carrier being the second power output terminal.

13. The power transmitting device of claim 12, wherein the output side sun gear includes a compound gear having first external teeth configured to engage with the output side planetary gear, and second external teeth configured to receive power transmitted from the input side carrier, the second external teeth having a greater diameter than the first external teeth.

14. The power transmitting device of claim 12, further comprising:
    a first connecting body configured to connect the input side carrier and the output side sun gear.

15. The power transmitting device of claim 12, wherein the input side ring gear has internal teeth configured to engage with the input side planetary gear, and external teeth configured to transmit power to the output side ring gear.

16. The power transmitting device of claim 12, further comprising:
    a second connecting body configured to connect the input side ring gear and the output side ring gear.

17. A motion assistance apparatus comprising:
a driving source configured to generate power;
a first supporting member configured to support a first portion of a user;
a second supporting member configured to support a second portion of the user;
a power transmitting frame connected to the second supporting member, the power transmitting frame configured to rotate relative to the first supporting member; and
a power transmitting device configured to transmit the power to the power transmitting frame, the power transmitting device including,
  an input side gear assembly including a first power input terminal and a plurality of first power output terminals;
  an output side gear assembly including a plurality of second power input terminals each configured to receive power from a respective one of the plurality of first power output terminals, and a second power output terminal configured to transmit the power to the power transmitting frame; and
  a stopper mechanism configured to select, for power transmission, one of a plurality of power transmitting paths connecting the plurality of first power output terminals and the plurality of second power input terminals, the stopper mechanism including a cam mechanism configured to rotate at least among a first position and a second position, the first position being a position in which the stopper mechanism engages with a first one of the plurality of second power input terminals and disengages from a second one of the plurality of second power input terminals, and the second position being a position in which the stopper mechanism is disengaged from the first one of the plurality of second power input terminals and engages with the second one of the plurality of second power input terminals.

18. A power transmitting device comprising:
a first gear assembly including a first input gear and a plurality of first output gears;
a second gear assembly including a plurality of second input gears and a second output gear, the plurality of second input gears and the plurality of first output gears configured to connect via a selected transmission path of a plurality of transmission paths between the plurality of first output gears and the plurality of second input gears, each of the plurality of transmission paths having a different gear ratio associated therewith; and
a cam connected to a stopping mechanism, the cam configured to rotate at least among a first position and a second position, the first position being a position in which the stopping mechanism engages with a first one of the plurality of second input gears and disengages from a second one of the plurality of second input gears, and the second position being a position in which the stopping mechanism is disengaged from the first one of the plurality of second input gears and engages with the second one of the plurality of second input gears.

19. A motion assistance apparatus comprising:
the power transmitting device of claim 18, the power transmitting device configured to provide an assistance force to portion of a user;
a sensor configured to sense motion information associated with motion of the user; and
a controller configured to determine one or more of a motion task and a desired torque level based on the motion information, and to adjust the assistance force by controlling the cam to move to one of the first position and the second position based on the one or more of the motion task and the desired torque level.

* * * * *